United States Patent [19]

Rattan

[11] 4,161,284
[45] Jul. 17, 1979

[54] SLOW DIFFUSER-AIR SCENT

[76] Inventor: Horace E. Rattan, P.O. Box 287, El Centro, Calif. 94423

[21] Appl. No.: 876,536

[22] Filed: Feb. 9, 1978

[51] Int. Cl.² .............................................. A24F 25/00
[52] U.S. Cl. .......................................... 239/43; 239/56
[58] Field of Search ............................. 239/34, 37–43, 239/53–59

[56] References Cited

U.S. PATENT DOCUMENTS

| | | | |
|---|---|---|---|
| 1,341,525 | 5/1920 | Vericel | 239/43 |
| 1,742,962 | 1/1930 | McCrosky | 239/55 |
| 1,865,700 | 7/1932 | Lichter | 239/43 X |
| 3,587,968 | 6/1971 | Hennart | 239/309 X |
| 3,727,840 | 4/1973 | Nigro | 239/57 X |

Primary Examiner—John J. Love

[57] ABSTRACT

A deodorant or fragrance dispensing packet for use in vehicles and the like is characterized by being quickly rechargable by squeezing the two parallel sides of the packet together, which causes spikes molded on the interior of one side of the packet container to rupture a liquid fragrance containing pod, permitting the perfume to flow into a surrounding absorbent pad from which the fragrance slowly evaporates and disseminates into the atmosphere through holes in the outer casing which were punched by the consumer after purchase to permit the dissemination of the first charge of fragrance which was contained in the absorbent pad.

4 Claims, 4 Drawing Figures

SLOW DIFFUSER-AIR SCENT

BACKGROUND OF THE INVENTION

The invention relates to deodorant or fragrance packets which are used in automobiles but may also be used in households or anywhere else where it is desired to freshen the air.

Because all air deodorant or fragrance devices operate on the principal of disseminating some substance into the air, any such substance or device will eventually dissipate all of its fragrance and lose its effectiveness. Although there have been developed deodorant packets or containers which are sealed until opened by the consumer to disseminate the fragrance, and some of these units are recapable or resealable to preserve the fragrance when it is not desired to use same, eventually all of these deodorant devices will dissipate all of the chemicals which create the fragrance and will become useless.

Although clearly one could recharge a fixed deodorant dispenser with pellets or a liquid frangrance indefinitely, there is a need for a device which can be very easily and effectively recharged and which accomodates the demand of Americans for absolute simplicity and convenience of operation without resorting to messy liquid refills or stocking a clutter of recharge capsules or pellets.

SUMMARY OF THE INVENTION

The present invention fulfills the above-mentioned need by providing a fragrance producing unit principally for use in vehicles which is sealed until opened by the consumer, upon which time a first charge of fragrance which has been absorbed in a pad is disseminated through punched openings in the semi-rigid walls of the enclosing container.

Upon the completion of the dissemination of the initial charge of fragrance, rupturing spike means protruding from one of the container walls are pressed into a pouch or pod containing fragrant liquid, thus permitting the liquid to drain out and recharge the absorbent pad surrounding the pod with fresh fragrant material, which once again disseminates slowly through the punched holes in the container to perfume the air.

The extreme simplicity and convenience of this single recharge technique is notable, and it is also significant that the simplistic means of recharging particularly adapts the deodorant packet for vehicular use where storage space, which for example could be used to store recharge material, is not readily available.

DETAILED DESCRIPTION OF THE PREFERRED EMBODIMENT

The deodorant of the instant invention could be provided in a variety of shapes and forms but in the preferred embodiment comprises a flattened container 10 composed of a semi-rigid plastic and being made from two molded half-shells 12 and 14 which are mated along a pressfitted seam 16 which is also preferably glued or welded so that the two shells define a completely sealed cavity 18 within.

Figure 1:
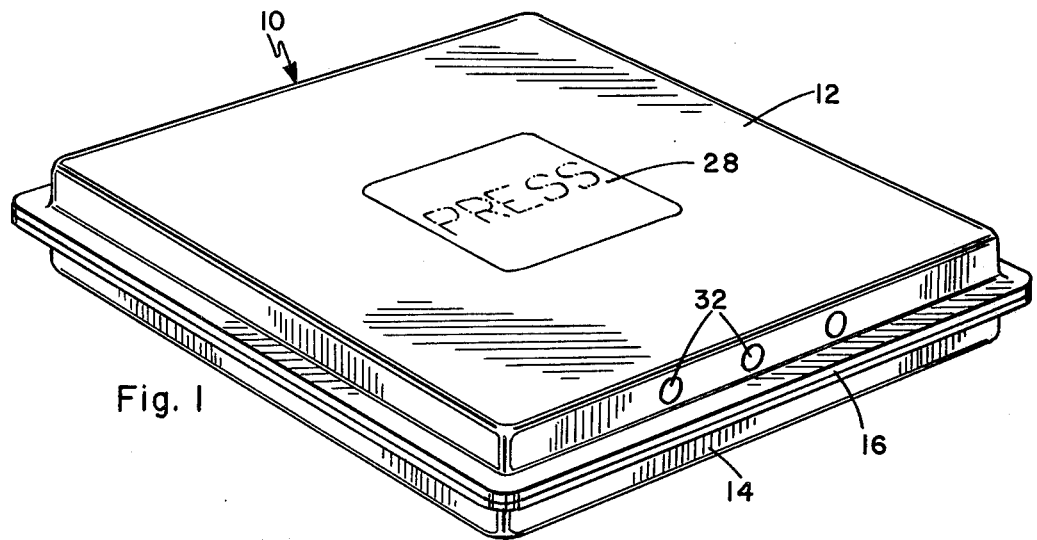
FIG. 1 is a perspective view of the deodorizer.
Figure 2:
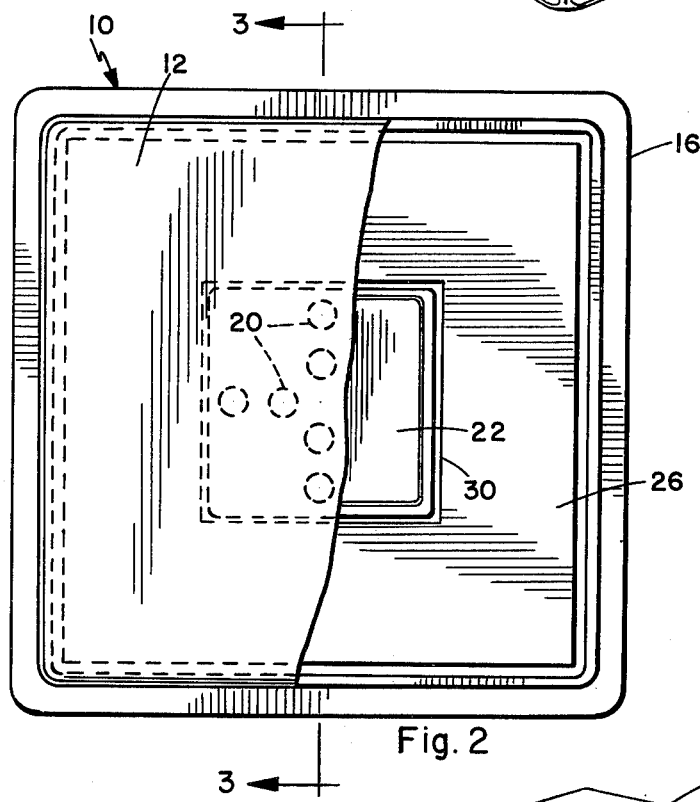
FIG. 2 is a top plan view, partially cut away.
Figure 3:
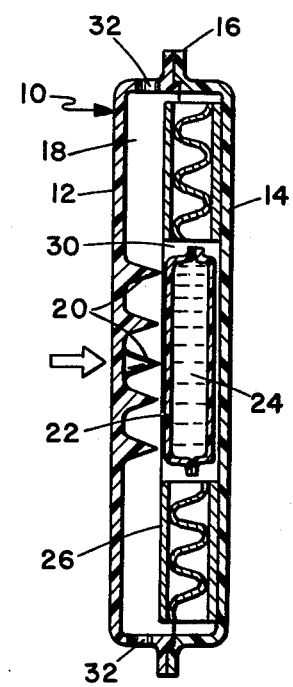
FIG. 3 is a sectional view taken on line 3—3 of FIG. 2.
Figure 4:
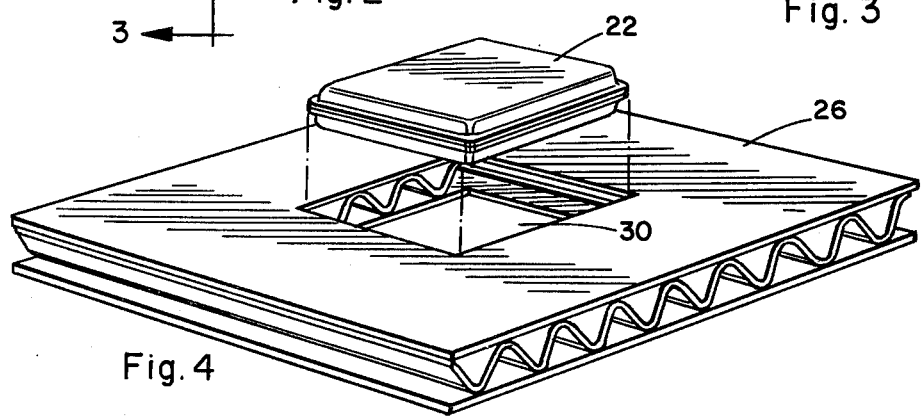
FIG. 4 is a perspective view of the absorbent insert and deodorant capsule.

The half-shell 12 serves as a mounting member for puncturing means which in the preferred embodiment are shown as spikes 20 which, as can be seen in FIG. 3, are juxtaposed to a pod 22 of fragrant liquid 24 and poised in such a way that when the centers of the two half-shells are compressed together such as indicated by the arrow in FIG. 3, the spikes rupture the liquid containing pod 22, thus freeing the liquid to flow into a pad 26 which surrounds the pod as can be seen in FIG. 2. To expedite the accomplishment of this operation an instruction may be molded into the half-shell as at 28, indicating "press", although a more lengthy instruction could easily be included.

The pod 22 is centered within the container 10 and maintained in this position by the surrounding pad 26 which, in the embodiment illustrated, is simply a stamped collar of corrugated fibreboard which has previously been impregnated with a fragrance, probably the same as that shown at 24. Clearly, the purpose of the pad 26 is to absorb the fragrant liquid and any material which would be suitably absorbent and form-retaining would also be suitable material for the compostion of the pad provided its cost were low. The pad could also extend across the width of the container and occupy substantially the entire volume of the cavity 18 save for that portion which defines the opening 30 in the pad which seats the pod 22.

It is to be preferred that when the illustrated unit is sold, the container 10 be completely hermetically sealed to contain the liquid fragrance which saturates the pad 26. However, ports are needed to permit the dissemination of the fragrance into the atmosphere once the unit is in its intended location, and a simple method of providing these ports is to mold a plurality of partial bores 32 in either one of the half-shells at virtually any position. These partial bores, shown in the drawings as being alongside the edge of half-shell 12, are opened into ports by jabbing through any sharp instruments thus permitting communication between the interior chamber 18 and the outside atmosphere. It is within the scope of the invention that these ports would be other than the simply manufactured open bores and that they incorporate means for recapping the packet if so desired to retain the fragrance from the pad between uses.

The operation of the unit, which should be fairly clear from the structural description above, is as follows. When sold, the container 10 is a sealed unit because the partial bores 32 have not yet been punctured and thus the fragrant liquid in the pad 26 will not dissipate. When desired to release the fragrance, the bores 32 are punctured completely through the wall of the container 10 and the unit is stationed in a vehicle or room, or anywhere else it is desired to freshen the air.

After a period of time, the strength of the fragrance will wane to the point that it is desired to recharge the pad 26 so that the entire unit is rejuvenated as mentioned above. This is accomplished by squeezing the two side walls of the container 10, forcing the spikes 20 into the rupturable deodorant containing pod 22, which then permits the liquid to flow out and saturate the partially or completely dried pad 26.

The above description and the drawings are indicative of the invention in its basic form, and it is contemplated that variations of this form such as providing multiple pods in different locations of the container, so that multiple recharges could be effected would fall within the scope of the appended claims. Also, structures along the same lines requiring repeated pressing to rupture sequential pods would also be within the ambit of the description and the appended claims.

The unit as described and claimed provides a novel deodorant packet which in effect has two complete lives, and can be recharged as described without having to resort to any type of refill solution or substance, and is thus ideally suited for vehicular use.

I claim:

1. A fragrance dispensing packet comprising:
   (a) an outer container having a pair of semi-rigid walls spaced apart to define a space therebetween;
   (b) a rupturable pod containing an evaporable fragrant substance disposed in said space;
   (c) at least one of said walls being yieldable adjacent said space;
   (d) at least one of said walls having an inwardly directed spike adjacent said pod to rupture same upon said walls being compressed together; and
   (e) an absorbent pad disposed in said container around said pod to retain same in said space and absorb the fragrant substance from said pod when same is ruptured.

2. Structure according to claim 1 wherein said pad is provided in frangrance-saturated condition and said outer container is sealed and has sealed ports openable to dissipate fragrance from said pad prior to said pod being punctured such that said packet is provided with separate, dual life spans.

3. Structure according to claim 2 wherein said ports comprise partial bores through said outer container which can be punched through with a sharp instrument when opening of the ports is desired.

4. Structure according to claim 1 wherein said pad is composed of corrugated fibreboard.

* * * * *